United States Patent [19]

Marrs et al.

[11] Patent Number: 4,672,856
[45] Date of Patent: Jun. 16, 1987

[54] SAMPLE SPLITTER

[75] Inventors: Gevan R. Marrs, Puyallup, Wash.; Kathryn A. Prieve, Thousand Oaks, Calif.

[73] Assignee: Weyerhaeuser Company, Tacoma, Wash.

[21] Appl. No.: 876,627

[22] Filed: Jun. 20, 1986

[51] Int. Cl.$^4$ .............................................. G01N 1/00
[52] U.S. Cl. .................................................. 73/863.52
[58] Field of Search ............ 73/863.41, 863.42, 863.43, 73/863.44, 863.45, 863.51, 863.52, 863.54, 863.55, 863.56, 863.57, 863.61

[56] References Cited

U.S. PATENT DOCUMENTS

| | | | |
|---|---|---|---|
| 850,293 | 4/1907 | Calkins | 73/863.52 |
| 2,379,921 | 7/1945 | Pizzirani et al. | 73/863.51 |
| 2,405,951 | 8/1946 | Herrold | 73/863.43 |
| 2,848,144 | 8/1958 | Haskell et al. | 73/863.45 |
| 3,472,079 | 10/1969 | Cordell | 73/863.51 |
| 3,942,388 | 3/1976 | Rathnow et al. | 73/863.43 |

FOREIGN PATENT DOCUMENTS

| | | | |
|---|---|---|---|
| 1049127 | 1/1959 | Fed. Rep. of Germany | 73/863.43 |
| 0709975 | 1/1980 | U.S.S.R. | 73/863.45 |

Primary Examiner—Jerry W. Myracle
Assistant Examiner—Robert R. Raevis

[57] ABSTRACT

The present invention is a sample splitter used to divide a larger sample of particulate material into representative smaller portions. The device uses a fixed conical sample splitter oriented with it apex upwards. Resting on this and translatable upwards is a sample receiving hopper. The hopper has open top and bottom ends. When receiving a sample to be divided, the bottom of the hopper rests on the splitter cone to form a sample retaining seal. When the hopper is raised, the sample falls by gravity around the splitter cone. An appropriately sized sample receiver located below the splitter cone receives the desired fraction. A generally cylindrical skirt is coaxially located below the splitter cone. The sample receiver is preferably a sector shaped drawer entering the skirt from the side.

5 Claims, 4 Drawing Figures

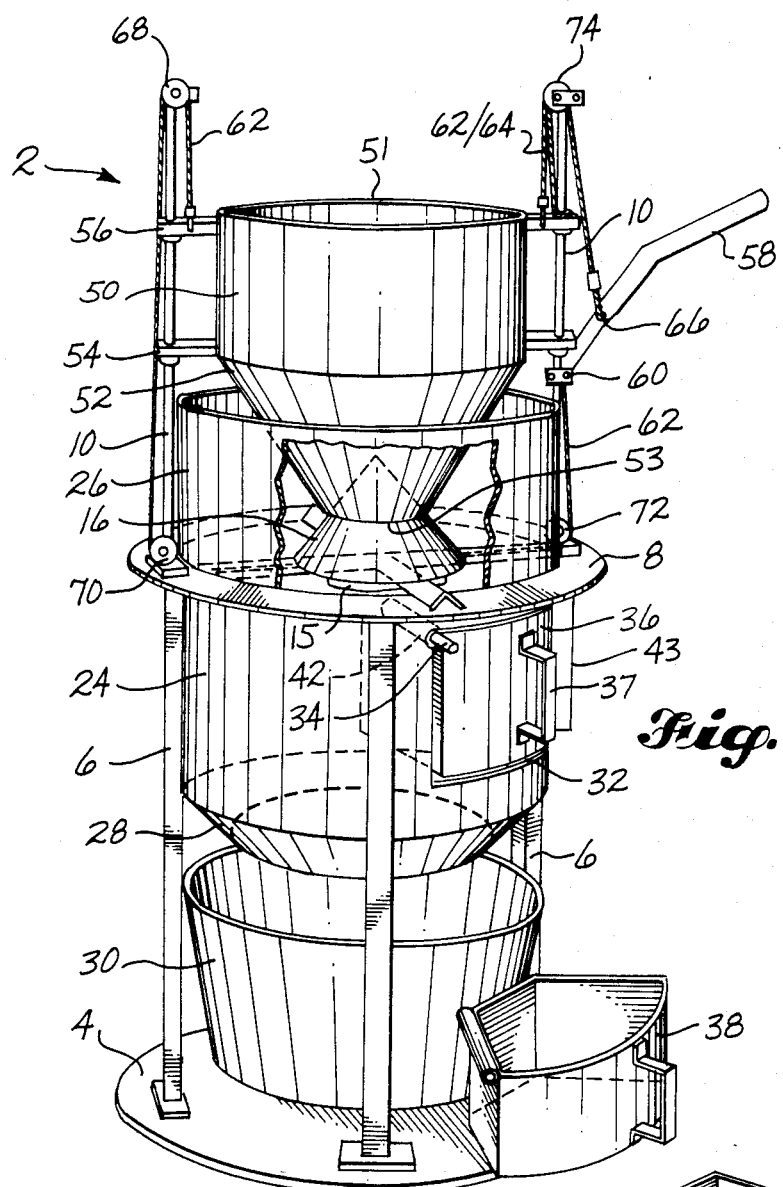
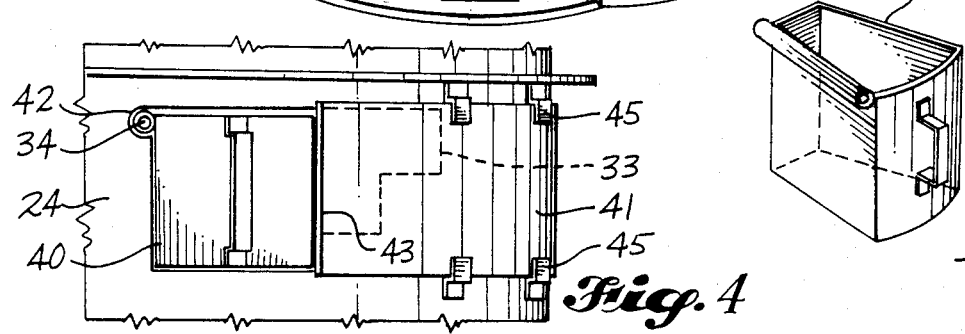

SAMPLE SPLITTER

BACKGROUND OF THE INVENTION

The present invention is a sample splitting device used to divide a larger sample of particulate material into representative smaller samples.

One of the most difficult problems in obtaining accurate analyses of granular or particulate materials resides in representative sampling of the product. Many products, such as ores, are sold on the basis of the amount of contained mineral materials. The price of other products, such as wood chips sold to pulp mills, is based on the dry weight of material contained within a naturally wet product. If pulp chips may be taken as an example, obtaining representative samples is extremely difficult because of the non-uniformity within the product itself. There is usually great variation in moisture content from point to point within a given shipment. The usual strategy used to deal with this problem is to take frequent samples. However, this frequently exceeds the ability of shippers or buyers to test the materials. It is, therefore, customary to blend an initial set of samples and remove a representative sub-sample for testing.

A good sample splitter should meet all of the following criteria: (1) the sub-sample must be representative: (2) the splitter should be easy and simple to use; (3) it should be easy to maintain and preferably have no electrically driven components so that it can be used at remote locations; (4) it should yield a consistently sized test sample in a single pass through the device, even when the initial samples vary substantially in size; (5) it should not lose any fine particles nor have any tendency to be plugged or bridged over by the larger ones.

There are a variety of sample dividing or splitting devices commercially available. None of these, until the time of the present invention, have been able to meet all of the above criteria.

Sample splitters have assumed a wide variety of forms. This variation may be readily seen by consulting the patent and technical literature in the field. One method of sample splitting involves pouring the material over a cone or pyramid. Fins or baffles associated with the cone then direct the sub-samples into bins. This method has a major deficiency due to difficulty in uniformly centering the sample over the cone when it is poured into the splitter. Considerable bias can be introduced when the sample is not accurately poured from a point directly above the projected axis of the cone. The most minor departure from uniform centering prior to the sample striking and passing the splitter cone will introduce inaccuracy. When samples are poured by hand it is almost impossible to avoid too much of the sample hitting one side of the cone.

The following U.S. patents are exemplary of attempts to overcome the above problem: Pizzirani et al, U.S. Pat. No. 2,379,921; Herrold, U.S. Pat. No. 2,405,951; Haskell et al, U.S. Pat. No. 2,848,144 and Rathnow et al, U.S. Pat. No. 3,942,338.

While the above sampling devices may be useful for the purpose intended, they all tend to be quite complex and are expensive or difficult to use. The present invention has fully overcome the above problems.

SUMMARY OF THE INVENTION

The present invention is a sample splitting device used to divide a larger particulate sample into representative smaller portions. It has a framework which supports the individual components of the device. Centered within the framework is fixed, generally conical sample splitter. The apex of the cone is oriented upwards and the cone is positioned so that the axis lies along a vertical line. The heart of the invention is a moveable, open bottom sample hopper mounted coaxially above the sample splitter. This hopper is translatable between a lower position and an upper position. At the lower position it is in contact with the splitter cone so as to form a seal which prevents material from passing between the two. In this position, the hopper defines a sample receiving and retaining volume. The hopper may be cylindrical, frustro-conical or of some other geometric form. The use of the hopper allows the sample entry point to be lower than would otherwise be possible if the hopper were fixed in position above the splitter cone. More importantly, it allows the entire composite sample to be loaded at one time. This way it can be uniformly centered prior to any of the sample passing by the splitter cone. This minimizes or eliminates the problem of operator-caused bias where too much of the sample is directed against one side of the cone.

A translating means attached to the frame is used to raise and lower the hopper. When the hopper is raised, the contained sample is released to fall by gravity around the splitter cone. A generally cylindrical skirt is mounted coaxially below the splitter cone to retain the falling sample particles. This skirt should have a diameter greater than the diameter of the splitter cone so that an annular space is present between them.

A sample receiver is mounted below the sample splitter and within the confines of the skirt. This receiver will have an open sample receiving area which is a predetermined fraction of the cross-sectional area of the skirt. In this manner, the desired portion of the sample being divided will fall into the sample receiver. One aspect of the invention is easy adaptability for the use of sample receivers of different sizes so that the sub-samples may be different fractions of the original sample. Thus, if a fixed size sample is required for testing, a larger fraction can be taken if the original sample is smaller than desired. The sample receivers are conveniently drawers which enter into the skirt below the splitter cone. These drawers may be sector shaped or preferably are in the form of a truncated sector. The truncated sector is especially suitable since the tip portion of a full sector would lie beneath the splitter cone and would not normally receive any of the descending particulate material.

It is an object of the present invention to provide a sample splitter which is simple in construction and operation and which will produce an accurate and representative sub-sample.

It is another object to provide a sample splitter which can simply and conveniently take sub-samples of different fraction sizes.

These and many other objects will become readily apparent to those skilled in the art upon reading the following description taken in conjunction of the drawings.

BRIEF DESCRIPTION OF THE DRAWINGS

FIG. 1 is a partially cut away overall perspective view of the sample splitter shown with a sample receiving drawer in place for taking a 1/6 fraction sample.

FIG. 4 is a partial side elevation showing an adaptation for sample receiving drawers of various sizes.

DESCRIPTION OF THE PREFERRED EMBODIMENTS

Figure 2:
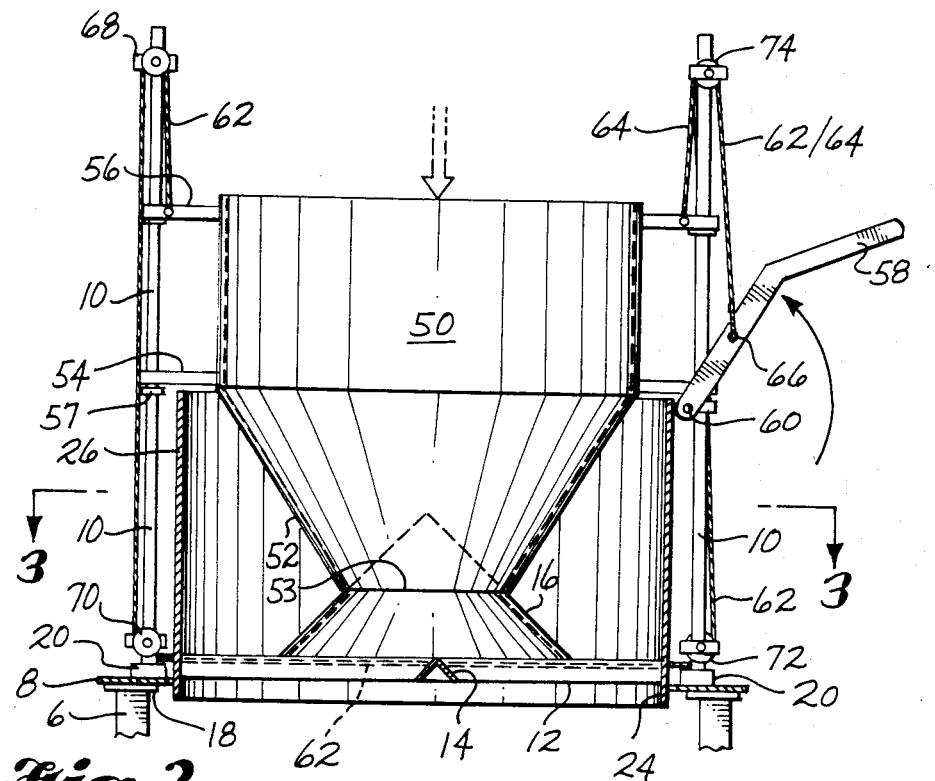
FIG. 2 is a side elevation of the upper portion of the sample splitter, partially cut away.
Figure 3:
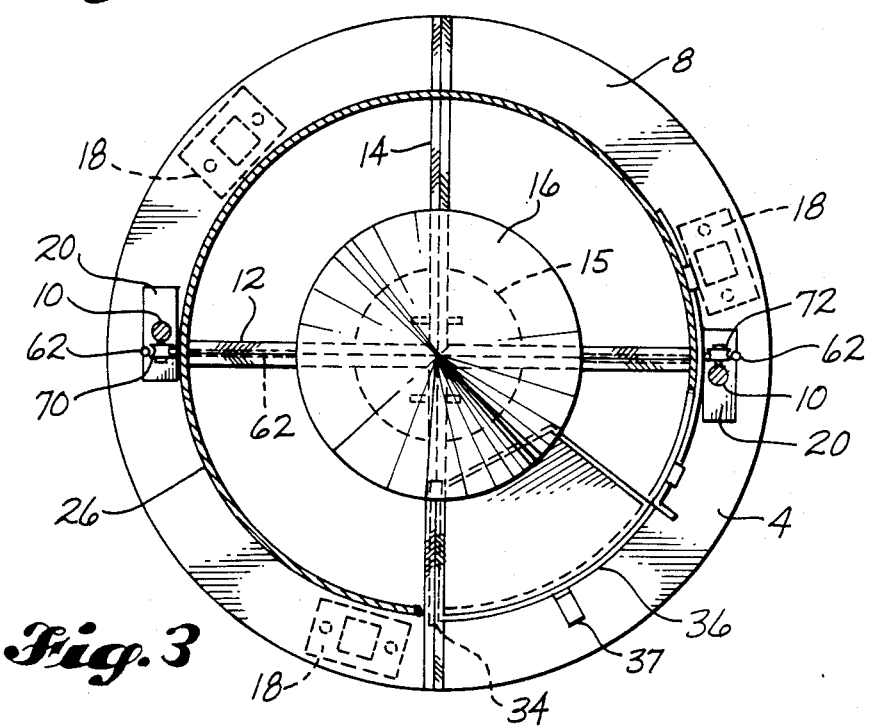
FIG. 3 is a top plan view along line 3—3 of FIG. 2, with most of the hopper mechanism removed and showing the 1/6 fraction sample receiving drawer in place.

Referring now to the drawings, FIG. 1 shows a general view of the sample splitter 2 with the hopper being in the lowered position ready to receive a sample. The splitter has an external frame which may have a base member 4, three leg members 6 and a mid or central section 8. Two hopper support bars 10 extend upward from the annular central portion 8. Two sample splitter support cross members 12, 14 have their ends anchored in central portion 8 and support the splitter cone 16 (FIGS. 2 and 3). These are preferably made of light angle iron with the apex or corner oriented upward. A disk 15 at the intersection of the cross members acts as a reinforcing gussett. Three brackets 18 on the lower surface of the annular central member 8 serve for attachment of the legs 6. In similar fashion, two brackets 20 on the upper surface of the annular mid-section support rods 10 for the hopper.

A cylindrical skirt 24 is coaxially located immediately beneath the sample splitter. It is desirable but not absolutely essential for the skirt to have an upper extension 26 surrounding the splitter cone and a lower funnel-shaped portion 28. This skirt serves to direct that portion of the sample not caught by the sub-sample receiver into a receptacle 30.

An opening 32 is formed in the side of the skirt serves for admission of the sample receiving drawer 36 having a handle 37. This opening may be made in step-wise fashion 33 to receive drawers of different widths or included angle. A drawer support rod 34 depends from gusset disk 15 at the junction of the cross support members 12 and 14. This engages a corresponding drawer glide tube 24 attached to one of the upper edges of the drawer. The lower edge of the drawer rests against the appropriate area in the cutout portion of the skirt. Drawer support rod 34 is preferably located directly below one of the angle iron cross members, in this case cross member 14, so that it will not be in an interfering position as the sample falls from the hopper.

A sliding door 41 (FIG. 4) with pull flange 43 may be mounted on skirt 24 in guides 45. This will prevent inadvertent sample spilling when the smaller drawers are being used.

The device is shown with a 60° included angle drawer in place for receiving a 1/6 fraction of the original sample. Alternate drawer 38 has an included angle of 90° and is sized to receive a ¼ fraction sample. Drawer 40 has an included angle of 45° and is configured to receive a ⅛ fraction sample.

The provision of a vertically translatable sample receiving hopper 50 is a key part of the present invention. Hopper 50 has an upper portion which is cylindrical in form and has an open upper end 51. The lower portion 52 of the hopper is frustro-conical in form and has an open lower end 53. In the lowered position, the lower end 53 of the hopper rests tightly against the sample splitter to cone to provide an adequate seal and prevent loss of any portion of the sample. Hopper guides 54, 56 are welded to the sides of the hopper. These are appropriately drilled to run freely on the hopper support bars 10. A stop or shock absorber 57 may alternatively be mounted on one or both of support bars 10.

The hopper is raised or lowered by an operating handle 58 which is pivoted to a bracket 60 mounted to one of the hopper support bars. Cables 62 and 64 are attached to upper hopper guide bar 56, or to some other convenient location. Left cables 62 passes over upper pulley 68 and lower pulley 70. Here it is directed under cross member 12 and upward around pulley 72 to a double pulley 74. From there it passes to an attachment point 66 on handle 58. The right cable 64 passes from its attachment point on the hopper guide around the double pulley 74 to common attachment point 66 on operating handle 58.

In operation the hopper is first moved to the lower position where it is resting against the splitter cone. A sample to divided is poured in and leveled if necessary. The hopper is then raised by the operating handle and the sample pours out by gravity over the splitter cone. The appropriate fraction is caught in the sample receiving drawer beneath while the bulk of the material falls into the collection tub.

EXAMPLE

A sample splitter for testing wood chips was designed and built as follows. A splitter cone was made from aluminum having an included angle of 90°, a base diameter of 305 mm and a height of 154 mm. The upper cylindrical portion of the movable hopper was about 460 mm in diameter and 200 mm in height. The lower opening frusto-conical lower portion of the hopper was about 180 mm in diameter where it contacted the splitter cone while the overall height of this portion was about 215 mm in height. The upper 60% of the splitter cone projected into the hopper when the hopper was resting against the cone. This low contact point helps significantly in improving splitting accuracy. The outside diameter of the cylindrical skirt enclosing the sample splitter was about 560 mm. The hopper could be raised about 150 mm about its resting point on the splitter cone. A splitter this size could accommodate a wood chip sample of approximately 5 kg (oven dry basis) having individual chips or splinters up to 130 mm long without bridging or jamming.

It will be evident to those skilled in the art that many departures could be made in the device just described that would be mechanically equivalent and would not depart from the spirit of the invention. The invention is thus to be considered as being limited only by the following claims.

We claim:

1. In a sample splitting device of the type used to divide a larger particulate sample into representative smaller portions, the improvement which comprises:
   a framework supporting the device;
   a fixed, generally conical, sample splitter having an upwardly oriented apex;
   a moveable, open bottom sample receiving hopper means mounted coaxially above the sample splitting means, said hopper means being translatable between a lower position and an upper position and being in contact with the sample splitter means when in the lower position so as to enclose a sample retaining volume, said sample being released to fall by gravity when the hopper means is moved to the upper position;

translating means attached to the frame to raise and lower the hopper means;

a generally cylindrical skirt means mounted coaxially below the sample splitter means to retain falling sample particles, said skirt means having a diameter greater than the diameter of the sample splitter means; and sample receving means mounted below the sample splitter means and within the skirt means, said receiving means having an open sample receiving area less than the cross sectional area of the skirt means to receive a predetermined fraction of the sample being divided.

2. The sample splitting device of claim 1 in which the sample receiving means is at least one drawer slideable into the skirt means.

3. The sample splitting device of claim 2 in which the sample receiving drawer is generally sector-shaped.

4. The sample splitting device of claim 1 in which the sample splitter means is a cone with an included angle of about 90°.

5. The sample splitter device of claim 1 in which the skirt means extends upward to enclose the sample splitter means.

* * * * *